(12) United States Patent
Raffle et al.

(10) Patent No.: US 9,116,545 B1
(45) Date of Patent: Aug. 25, 2015

(54) INPUT DETECTION

(76) Inventors: Hayes Solos Raffle, Palo Alto, CA (US);
Cliff L. Biffle, Berkeley, CA (US)

(*) Notice: Subject to any disclaimer, the term of this patent is extended or adjusted under 35 U.S.C. 154(b) by 256 days.

(21) Appl. No.: 13/425,830

(22) Filed: Mar. 21, 2012

(51) Int. Cl.
*G09G 5/00* (2006.01)
*G06F 3/01* (2006.01)
*G02B 27/01* (2006.01)
*A61B 3/113* (2006.01)

(52) U.S. Cl.
CPC ............... *G06F 3/013* (2013.01); *A61B 3/113* (2013.01); *G02B 27/017* (2013.01); *G02B 2027/0138* (2013.01); *G02B 2027/0187* (2013.01)

(58) Field of Classification Search
CPC .. G06F 3/013; G02B 27/017; G02B 27/0187; G02B 2027/0138; A61B 3/113
USPC .......... 345/8, 156; 351/209–210; 348/E7.085
See application file for complete search history.

(56) References Cited

U.S. PATENT DOCUMENTS

| 4,081,623 | A |   | 3/1978  | Vogeley |         |
|-----------|---|---|---------|---------|---------|
| 5,360,971 | A |   | 11/1994 | Kaufman |         |
| 5,570,151 | A |   | 10/1996 | Terunuma|         |
| 5,621,424 | A |   | 4/1997  | Shimada |         |
| 5,926,655 | A |   | 7/1999  | Irie    |         |
| 5,991,085 | A | * | 11/1999 | Rallison et al. | 359/630 |
| 6,091,546 | A | * | 7/2000  | Spitzer | 359/618 |
| 6,163,281 | A | * | 12/2000 | Torch   | 341/21  |
| 6,369,952 | B1 | * | 4/2002 | Rallison et al. | 359/630 |
| 6,542,081 | B2 | * | 4/2003 | Torch   | 340/575 |
| 6,920,283 | B2 |   | 7/2005 | Goldstein |       |
| 7,192,136 | B2 |   | 3/2007 | Howell et al. |   |
| RE39,539  | E  | * | 4/2007 | Torch   | 340/575 |
| 7,255,437 | B2 |   | 8/2007 | Howell et al. |   |
| 7,347,551 | B2 |   | 3/2008 | Fergason et al. | |
| 7,380,936 | B2 |   | 6/2008 | Howell et al. |   |
| 7,401,918 | B2 |   | 7/2008 | Howell et al. |   |
| 7,401,920 | B1 | * | 7/2008 | Kranz et al. | 351/210 |

(Continued)

FOREIGN PATENT DOCUMENTS

| JP | 2011221890 | 11/2011 |
|----|------------|---------|
| WO | 2011114092 | 9/2011  |

OTHER PUBLICATIONS

T. Arias, "Relation Between Intensity and Amplitude", Sep. 13, 2001.

(Continued)

*Primary Examiner* — Lun-Yi Lao
*Assistant Examiner* — Peter D McLoone
(74) *Attorney, Agent, or Firm* — McDonnell Boehnen Hulbert & Berghoff LLP

(57) ABSTRACT

Example methods and systems determine viewing states, blinks, and blink intervals of an eye of a wearer of a head-mountable device. The head-mountable display can emit IR radiation from an associated IR radiation source toward a target location. An IR sensor associated with the head-mountable display can receive reflected IR radiation, such as the IR radiation emitted by the IR radiation source and reflected from the target location. The IR sensor can generate amplitude data for the reflected IR radiation. The head-mountable display can be used to determine a viewing state of the target location. The viewing state can be based on the amplitude data. The viewing state can determined from among a no-wearer-present viewing state, a wearer-present viewing state, a closed-eye viewing state, an open-eye viewing state, a non-display-viewing viewing state, and a display-viewing viewing state.

18 Claims, 11 Drawing Sheets

(56) References Cited

U.S. PATENT DOCUMENTS

| | | | |
|---|---|---|---|
| 7,438,410 B1 | 10/2008 | Howell et al. | |
| 7,481,531 B2 | 1/2009 | Howell et al. | |
| 7,500,746 B1 | 3/2009 | Howell et al. | |
| 7,500,747 B2 | 3/2009 | Howell et al. | |
| 7,515,054 B2 | 4/2009 | Torch | |
| 7,543,934 B2 | 6/2009 | Howell et al. | |
| 7,581,833 B2 | 9/2009 | Howell et al. | |
| 7,621,634 B2 | 11/2009 | Howell et al. | |
| 7,677,723 B2 | 3/2010 | Howell et al. | |
| RE41,376 E * | 6/2010 | Torch | 340/575 |
| 7,760,898 B2 | 7/2010 | Howell et al. | |
| 7,762,665 B2 * | 7/2010 | Vertegaal et al. | 351/209 |
| 7,771,046 B2 | 8/2010 | Howell et al. | |
| 7,784,945 B2 | 8/2010 | Sugiyama | |
| 7,792,552 B2 | 9/2010 | Thomas et al. | |
| 7,806,525 B2 | 10/2010 | Howell et al. | |
| 7,922,321 B2 | 4/2011 | Howell et al. | |
| 8,073,198 B2 | 12/2011 | Marti | |
| 8,109,629 B2 | 2/2012 | Howell et al. | |
| 8,235,529 B1 * | 8/2012 | Raffle et al. | 351/209 |
| 8,363,098 B2 * | 1/2013 | Rosener et al. | 348/77 |
| 8,428,053 B2 * | 4/2013 | Kannappan | 370/356 |
| 8,506,080 B2 * | 8/2013 | Raffle et al. | 351/209 |
| 8,593,570 B2 * | 11/2013 | Boland et al. | 348/376 |
| 8,760,310 B2 * | 6/2014 | Rosener | 340/686.1 |
| 2001/0028309 A1 * | 10/2001 | Torch | 340/575 |
| 2004/0119814 A1 * | 6/2004 | Clisham et al. | 348/14.08 |
| 2004/0183749 A1 * | 9/2004 | Vertegaal | 345/7 |
| 2005/0007552 A1 * | 1/2005 | Fergason et al. | 351/210 |
| 2005/0264527 A1 | 12/2005 | Lin | |
| 2006/0103591 A1 * | 5/2006 | Tanimura et al. | 345/8 |
| 2006/0115130 A1 * | 6/2006 | Kozlay | 382/117 |
| 2006/0192775 A1 * | 8/2006 | Nicholson et al. | 345/211 |
| 2007/0024579 A1 | 2/2007 | Rosenberg | |
| 2007/0086764 A1 | 4/2007 | Konicek | |
| 2007/0201847 A1 | 8/2007 | Lei | |
| 2008/0211768 A1 | 9/2008 | Breen | |
| 2009/0195497 A1 | 8/2009 | Fitzgerald et al. | |
| 2010/0066821 A1 * | 3/2010 | Rosener et al. | 348/77 |
| 2010/0079356 A1 * | 4/2010 | Hoellwarth | 345/8 |
| 2010/0109895 A1 * | 5/2010 | Rosener | 340/686.1 |
| 2010/0118158 A1 * | 5/2010 | Boland et al. | 348/211.2 |
| 2010/0149073 A1 * | 6/2010 | Chaum et al. | 345/8 |
| 2010/0215170 A1 * | 8/2010 | Kannappan | 379/418 |
| 2010/0235667 A1 | 9/2010 | Mucignat et al. | |
| 2011/0115878 A1 * | 5/2011 | Noteware et al. | 348/14.12 |
| 2011/0231757 A1 | 9/2011 | Haddick et al. | |
| 2012/0019645 A1 | 1/2012 | Maltz | |
| 2012/0019662 A1 | 1/2012 | Maltz | |
| 2013/0128067 A1 * | 5/2013 | Boland et al. | 348/211.2 |
| 2013/0135204 A1 * | 5/2013 | Raffle et al. | 345/158 |
| 2013/0176533 A1 * | 7/2013 | Raffle et al. | 351/209 |
| 2013/0257709 A1 * | 10/2013 | Raffle et al. | 345/156 |
| 2013/0300652 A1 * | 11/2013 | Raffle et al. | 345/156 |
| 2014/0101608 A1 * | 4/2014 | Ryskamp et al. | 715/810 |
| 2014/0161412 A1 * | 6/2014 | Chase et al. | 386/224 |
| 2014/0184729 A1 * | 7/2014 | Noteware et al. | 348/14.08 |

OTHER PUBLICATIONS

M. Chau et al.,"Real Time Eye Tracking and Blink Detection with USB Cameras", Boston University Technical Report No. 2005-12, May 12, 2005.

College of Engineering at the University of Wisconsin-Madison, "Device May Help Prevent 'Falling Asleep at the Switch'", Jan. 27, 1997.

Digi-Key Corporation,"Order Page for Silicon Laboratories SI1143-A10-GMR", Mar. 15, 2012.

M. Eizenmann et al., "Precise Non-Contacting Measurement of Eye Movements Using the Corneal Reflex", Vision Research, vol. 24, Issue 2, pp. 167-174, 1984.

Silicon Labs, "Si1102 and Si1120 Designers Guide", Rev 0.1, Oct. 2009, Silicon Laboratories.

Silicon Labs, "Si1143 Proximity/Ambient Light Sensor with IA2C Interface", Nov. 19, 2010, Silicon Laboratories.

M. A. Tinker, "Apparatus for Recording Eye-Movements", The American Journal of Psychology, Jan. 1931, pp. 115-118, vol. 43, No. 1, University of Illinois Press.

Miluzzo et al., "EyePhone: Activating Mobile Phones with your Eyes", MobiHeld 2010 Proceedings of the Second ACM SIGCOMM Workshop on Networking, Systems and Applications on Mobile Handhelds, Aug. 30, 2010, pp. 15-20, published by Association for Computing Machinery, New York, NY, USA.

* cited by examiner

| Eye Position 210 | IR Intensity 220 | Viewing State 230 |
|---|---|---|
|  144 — 162, HMD TL 210a 100 | Zero to relatively very low 220a | No wearer present 230a |
|  100, Gaze 212b, 162, Eye 214b, TL 210b | Relatively low 220b | Wearer present and looking at display 230b |
|  100, Gaze 212c, 162, Eye 214c, TL 210c | Relatively moderate 220c | Wearer present and not looking at display 230c |
|  100, TL 210d, 162, Eye 214d | Relatively high 220d | Wearer present with eye closed 230d |

INPUT DETECTION

BACKGROUND

Unless otherwise indicated herein, the materials described in this section are not prior art to the claims in this application and are not admitted to be prior art by inclusion in this section.

Computing devices such as personal computers, laptop computers, tablet computers, cellular phones, and countless types of Internet-capable devices are increasingly prevalent in numerous aspects of modern life. Over time, the manner in which these devices are providing information to users is becoming more intelligent, more efficient, more intuitive, and/or less obtrusive.

The trend toward miniaturization of computing hardware, peripherals, as well as of sensors, detectors, and image and audio processors, among other technologies, has helped open up a field sometimes referred to as "wearable computing." In the area of image and visual processing and production, in particular, it has become possible to consider wearable displays that place a very small image display element close enough to a wearer's (or user's) eye(s) such that the displayed image fills or nearly fills the field of view, and appears as a normal sized image, such as might be displayed on a traditional image display device. The relevant technology may be referred to as "near-eye displays."

Near-eye displays are fundamental components of wearable displays, also sometimes called "head-mountable displays" (HMDs). A head-mountable display can place a graphic display or displays close to one or both eyes of a wearer. To generate the images on a display, a computer processing system may be used. Such displays may occupy a wearer's entire field of view, or only occupy part of wearer's field of view. Further, head-mountable displays may be as small as a pair of glasses or as large as a helmet.

Emerging and anticipated uses of wearable displays include applications in which users interact in real time with an augmented or virtual reality. Such applications can be mission-critical or safety-critical, such as in a public safety or aviation setting. The applications can also be recreational, such as interactive gaming.

SUMMARY

In one aspect, an example method can include: (a) emitting infrared (IR) radiation from an IR radiation source associated with a head-mountable display toward a target location, (b) receiving, at an IR sensor associated with the head-mountable display, reflected IR radiation, wherein the reflected IR radiation includes IR radiation emitted by the IR radiation source and reflected from the target location, (c) generating amplitude data for the reflected IR radiation received at the IR sensor, and (d) determining, based on the amplitude data and using the head-mountable display, a viewing state of the target location using the head-mountable display, from among a no-wearer-present viewing state, a wearer-present viewing state, a closed-eye viewing state, an open-eye viewing state, a non-display-viewing viewing state, and a display-viewing viewing state.

In another aspect, an article of manufacture can include a non-transitory computer-readable medium having instructions stored thereon. Upon execution of the instructions by a computing device, the instructions can cause the computing device to perform functions. The functions can include: (a) emitting infrared (IR) radiation from an IR radiation source associated with a head-mountable display toward a target location, (b) receiving reflected IR radiation, where the reflected IR radiation includes IR radiation emitted by the IR radiation source and reflected from the target location, (c) generating amplitude data for the reflected IR radiation, and (d) determining, based on the amplitude data, a viewing state of the target location from among a no-wearer-present viewing state, a wearer-present viewing state, a closed-eye viewing state, an open-eye viewing state, a non-display-viewing viewing state, and a display-viewing viewing state.

In yet another aspect, a head-mountable device can include: an infrared (IR) radiation source, an IR sensor, and a processor. The IR radiation source can be configured to emit IR radiation toward a target location. The IR sensor can be configured to receive IR radiation reflected from the target location and to generate amplitude data for the reflected IR radiation. The processor can be configured to: (a) receive the amplitude data, and (b) determine, based on the amplitude data, a viewing state of the target location using the head-mountable display, from among a no-wearer-present viewing state, a wearer-present viewing state, a closed-eye viewing state, an open-eye viewing state, a non-display-viewing viewing state, and a display-viewing viewing state.

These as well as other aspects, advantages, and alternatives, will become apparent to those of ordinary skill in the art by reading the following detailed description, with reference where appropriate to the accompanying drawings.

DETAILED DESCRIPTION

Introduction

Figure 1A:
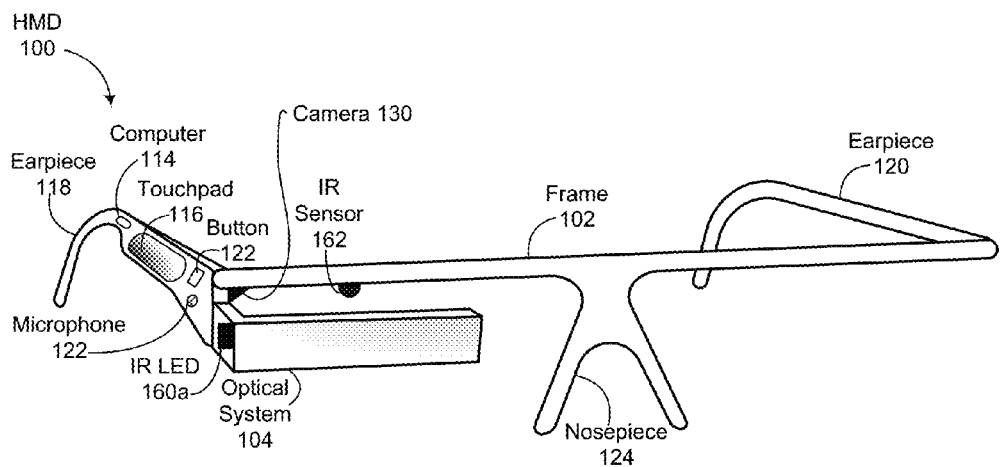
FIG. 1A is a perspective view illustrating a head mountable display configured to determine eye positions, according to an example embodiment.

Devices, such as head-mountable displays (HMDs), can benefit from the use of gaze detection. For example, a HMD can be configured to respond to a wearer only when the wearer is looking at the display portion of the HMD. In particular, a simple, low-cost, low-power solution to determine when the wearer is "proximate" (i.e., when the wearer is wearing the HMD and/or looking at the display portion) is beneficial, as HMDs often have limited resources for operation, including power.

One solution to the proximate wearer problem is to analyze the signal of a light-emitting diode (LED) that emits from the display portion and is reflected at a "target location", or position to readily view the display portion of the HMD, toward a sensor. For example, the LED can emit infra-red (IR) radiation that can be reflected off an eye of a wearer at the target location and then detected by an IR sensor. IR radiation has the advantages of both not being visible by the wearer and not causing damage to the wearer's eye.

When IR radiation is emitted from the HMD, it can be reflected from an object, such as an eye of a wearer, at the target location. However, when the HMD is not being worn, an eye or other object is not present at the target location to reflect IR radiation. Thus, little or no IR radiation is likely to be reflected.

When an eye is present at the target location, some IR radiation will be absorbed and some IR radiation will be reflected. When the eye at the target location is looking at the display portion, much of the IR radiation is reflected from darker portions of the eye, such as the pupil and iris. These darker portions of the eye absorb more radiation than lighter portions of the eye, such as the sclera or white of the eye. As such, a lesser amount of reflected radiation is observed when the eye is looking at the display portion than when the eye is looking away from the display portion.

When the eye at the target location is closed, the eyelid can reflect the IR radiation. The eyelid is a better reflector of IR radiation than the surface of the eye, and so more IR radiation is reflected when the eye is closed than when open. Thus, an IR sensor would observe an increase in IR radiation when the eye is closed relative to when the eye is open.

Based on these observations, the computing device can receive IR intensity data from the IR sensor to determine a viewing state of the eye. Example viewing states include: no-wearer-present, wearer-present, closed-eye, open-eye, non-display-viewing, and display-viewing states. Other viewing states are possible as well. In scenarios where sensors are used on both eyes of a wearer, the indications from the two eyes can be combined to determine if both eyes are simultaneously looking at an object, both eyes are closed, or are in different positions (e.g., winking).

These techniques can also sense blinking of the wearer, because the eyelid is more reflective than the iris. In these embodiments, intentional blinks can be used as inputs (e.g., "one blink for yes, two blinks for no"), as they differ in some measure, such as duration, than unintentional blinks. As such, the HMD can determine a blinking state as well as, or separately from, the viewing state.

Viewing states, blinking states, and/or changes of viewing and/or blinking state can be used to generate signals/commands to change a state of a user interface (UI). Example UI state change commands include commands to start/stop the display light source, take a photo, start/stop video and/or audio recording etc. For example, to operate a video camera associated with the HMD: the HMD could be in display-viewing viewing state to take video, transition to pause the video during a non-display-viewing viewing state, toggle audio recording based on observing intentional blinks, and quit recording when a no-wearer-present state is observed. Many other examples are possible as well.

Example Head Mountable Displays

FIG. 1A is a perspective view illustrating a head mountable display (HMD) 100 configured to determine eye positions. FIG. 1A shows HMD 100 with frame 102, nosepiece 124, and earpieces 118 and 120, which can be configured to secure the HMD 100 to a wearer's face via a wearer's nose and ears. For computational, input, and output purposes, the HMD 100 can include a computer 114, a touch pad 116, a microphone 122, a button 124, a camera 130, and an optical system 104. The optical system 104 could be attached to the frame 102 and can be formed of any material that can suitably display a projected image or graphic.

Figure 1B:
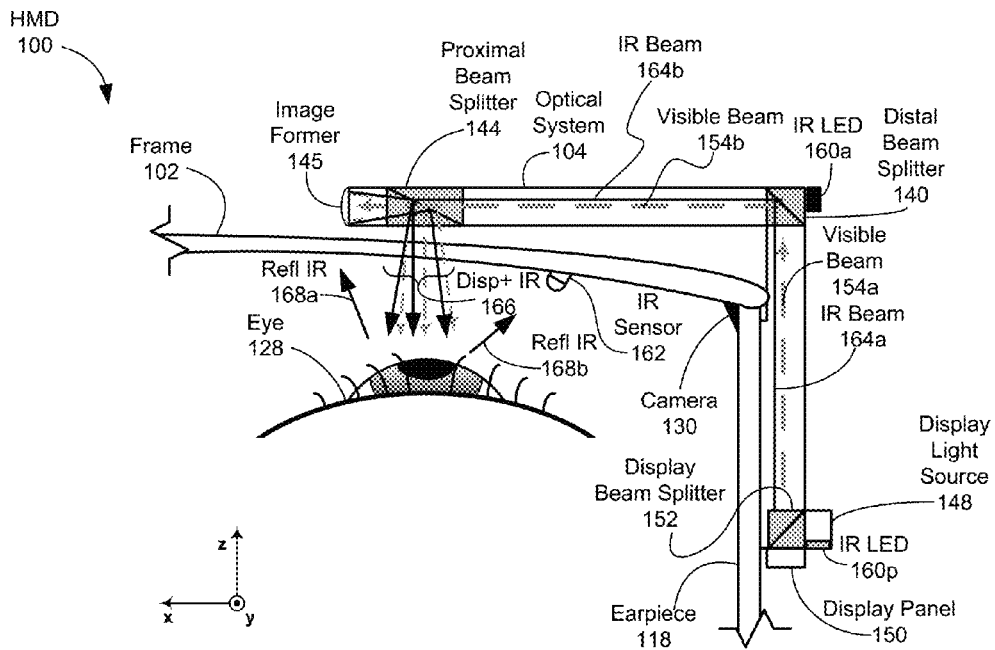
FIG. 1B is a top view of the head mountable display of FIG. 1A while in use, according to an example embodiment.

Additionally, FIG. 1A shows the optical system 104 of HMD 100 with an eye-proximity system formed by IR LED 160a and IR sensor 162. The eye-proximity system can be configured to determine proximity to one of the wearer's eyes. The IR LED can be either externally mounted to a display path, as shown at position 160a in both FIGS. 1A and 1B, or can be integrated within a light source of the optical system, such as shown in FIG. 1B at position 160p as part of display light source 148. An example implementation of IR sensor 162 can include a single-chip proximity sensor system that provide integrated functionality on a single chip, such as the SI1143-A10-GMR which provides high frequency strobing of multiple LEDs, analysis of the signals, and communication of signal amplitudes to a computer or controller, such as computer 114. In some embodiments, multiple IR LEDs 160a/160p and/or IR sensors 162 can be utilized.

FIG. 1B is a top view of HMD 100 illustrated in FIG. 1A while in use. FIG. 1B shows optical system 104 of HMD 100 with distal beam splitter 140, display light source 148, a display panel 150, a display beam splitter 152, a proximal beam splitter 144, and an image former 145. The display panel 150 could be configured to generate a light pattern from which virtual and/or real images could be formed. The display light source 148 may include, for example, one or more light-emitting diodes (LEDs) and/or laser diodes. The light pattern generated by the display panel 150 can be monochromatic or include multiple colors (such as red, green, and blue) to provide a color gamut for the virtual and/or real images. In embodiments where IR LED 160p is integrated with display light source 148, display light source 148 can generate both visible and infrared light. Additionally, FIG. 1B shows optical system 104 including eye proximity system with IR LED at either 160a or 160p and IR sensor 162.

In operation, visible light generated by display light source 148 can be guided by display beam splitter 152 toward distal beam splitter 140. Distal beam splitter 140 can substantially reflect the received light towards the proximal beam splitter 144 and then, to image former 145. Image former 145 can include a concave mirror or other optical component that forms a virtual image that is viewable through the proximal beam splitter 144. In this manner, a viewable image can be delivered to a target location for viewing by HMD wearer's eye 128.

Infrared light or radiation emitted by an IR LED at position 160p follows a common path with the visible light described in the paragraph immediately above to reach eye 128. When an IR LED is at position 160a, some of the infrared light or radiation emitted by the IR LED can reach eye 128 via using distal beam splitter 140, proximal beam splitter 144, and image former 145. These pathways of infrared light are shown as IR beams 164a, 164b using black coloration in FIG. 1B while pathways of visible light are shown as visible beams 154a, 154b using grey coloration in FIG. 1B.

After being reflected by proximal beam splitter 144, both visible and infrared light is directed toward eye 128, where some of both types of light can reflect from the surface of eye 128. Some of the infrared light or radiation can be received at sensor 162 as an infrared signal. In response, sensor 162 can generate amplitude data for the received infrared signal and transmit the amplitude data to computer 114.

Figure 1C:
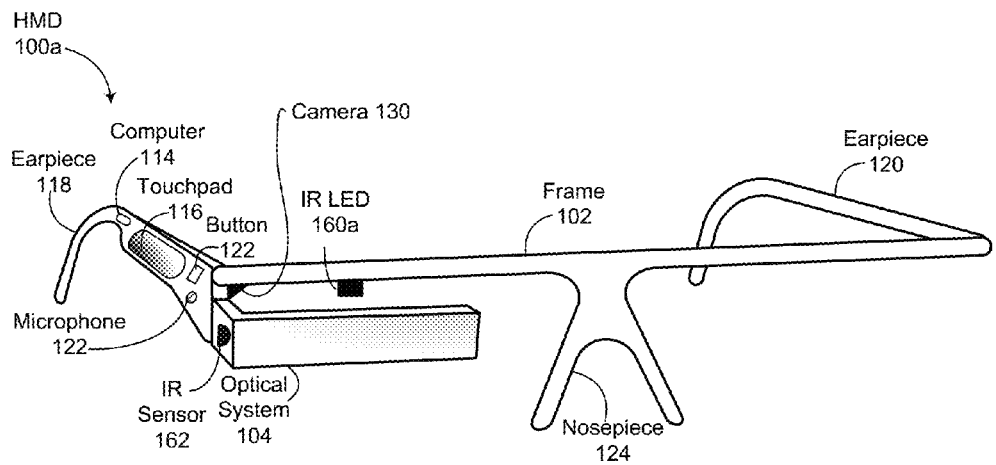
FIG. 1C is a perspective view illustrating another embodiment of a head mountable display configured to determine eye positions, according to an example embodiment.

FIG. 1C is a perspective view illustrating a HMD 100a configured to determine eye positions. In comparison to head mountable display 100, IR LED 160a and IR sensor 162 have switched positions. That is, IR LED 160a of HMD 100a is mounted in the position of IR sensor 162 of HMD 100, and IR sensor 162 of HMD 100a is mounted in the position of IR LED 160a of HMD 100. All other components of HMD 100 and HMD 100a are the same.

Figure 1D:
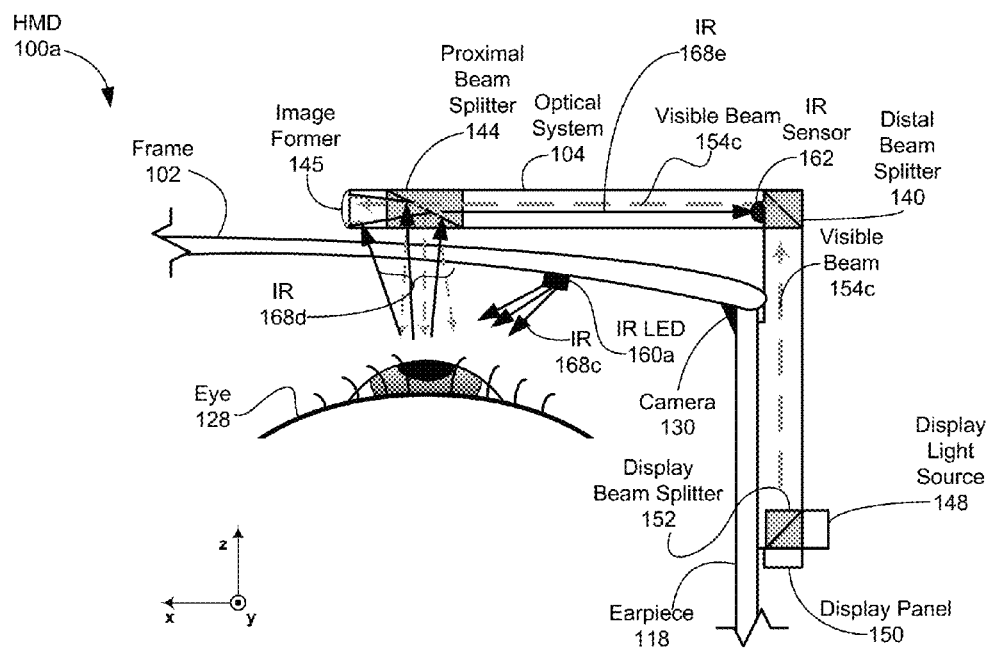
FIG. 1D is a top view of the head mountable display of FIG. 1C while in use, according to an example embodiment.

FIG. 1D is a top view of HMD 100a illustrated in FIG. 1C while in use. Visible light in HMD 100d travels the same path through optical system 104 to the target location as discussed above in the context of FIG. 1B. However, in HMD 100a, infrared light or radiation does not travel the same path as the infrared light or radiation does in HMD 100. Rather, in HMD 100a, IR light or radiation travels from IR LED 160a as IR 168c toward the target location. At the target location, FIG. 1D shows IR 168c reflected from of eye 128 as IR 168d directed toward proximal beam splitter 144. Upon reaching proximal beam splitter, reflected IR light 168e travels as shown in FIG. 1D toward IR sensor 162. As infrared light or radiation 168e can be received at IR sensor 162 as an infrared signal. In response, IR sensor 162 can generate amplitude data for the received infrared signal and transmit the amplitude data to computer 114.

Amplitude data can be processed by computer 114 (or another computing device). Computer 114 can use calibration data to compare input signal amplitudes from calibration data to determine a "viewing state". Example viewing states for HMD 100 or HMD 100a are indicated in Table 1 below.

TABLE 1

| Viewing State | IR radiation Received at IR Sensor |
|---|---|
| No-wearer-present | No measurable IR radiation received |
| Wearer-present | Measurable IR radiation received |
| Closed-eye | IR radiation reflected from a closed eye |
| Open-eye | IR radiation reflected from an open eye |
| Non-display-viewing | IR radiation reflected from an open eye not looking at HMD |
| Display-viewing | IR radiation reflected from an open eye looking at HMD |

Example Determinations of Viewing States

Figure 2:
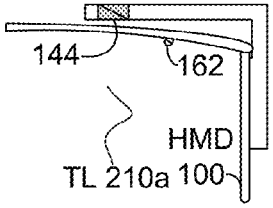
FIG. 2 is a table relating eye positions, intensity values, and viewing states according to an example embodiment.
Figure 2:
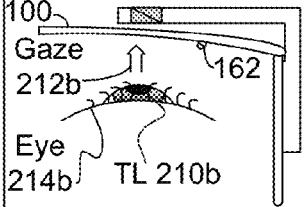
Figure 2:
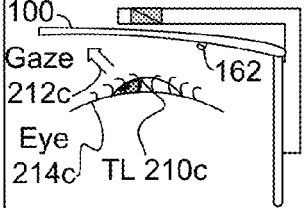
Figure 2:
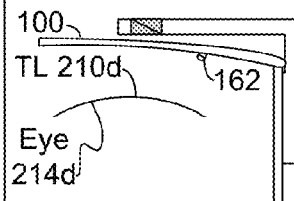

FIG. 2 shows table 200 relating eye positions, intensity values, and viewing states according to an example embodiment. Table 200 has three columns: eye position 210, IR intensity 220, and viewing state 230. Each row of table 200 identifies a particular eye position and corresponding IR intensity and viewing state(s) of HMD 100. In other embodiments not shown in the Figures, HMD 100a can replace HMD 100.

FIG. 2 shows the first non-heading row of table 200 with target location 210a shown with respect to head-mountable device 100 that depicts proximal beam splitter 144, and IR sensor 162. As no eye is shown at target location 210a, such as when a wearer has taken off head mountable device 100, it is likely that no object will reflect IR radiation emitted from proximal beam splitter 144 toward IR sensor 162. Thus, when no eye is at target location ("TL") 210a, the observed IR intensity 220a at IR sensor 162 is relatively very-low or perhaps zero. Based on a relatively very-low IR or zero observed intensity, a viewing state can be determined to be viewing state 230a of "No wearer present."

The second non-heading row of table 200 shows eye 214b at target location 210b wearing head mountable device 100 and looking at proximal beam splitter 144. A portion of eye 214b looking directly at proximal beam splitter 144 is a relatively dark portion of the eye, including the pupil, which is black, and the iris, which is most frequently darker than the surrounding sclera. That is, IR radiation reflected to IR sensor 162 will be greater when a wearer is looking at proximal beam splitter 144 than when no wearer is present, but will be relatively low. Thus, when an eye is at target location 210b, the observed IR intensity 220b at IR sensor 162 is relatively low. Based on a relatively low IR intensity, a viewing state can be determined to be a viewing state 230b of "Wearer present and looking at display."

The third non-heading row of table 200 shows eye 214c at target location 210c wearing head mountable device 100 and looking away from proximal beam splitter 144, as indicated via gaze 212c. A portion of eye 214c directly under proximal beam splitter 144 is a relatively light portion of the eye, partially or completely including sclera. IR radiation reflected to IR sensor 162 will be greater than when a wearer is looking directly at proximal beam splitter 144, but will be lower than when an eye is present and closed. Thus, when an eye is at eye position 210c, the observed IR intensity 220c at IR sensor 162 is relatively moderate. Based on a relatively moderate IR intensity, a viewing state can be determined to be a viewing state 230c of "Wearer present and not looking at display."

The third non-heading row of table 200 shows closed eye 214d at target location 210d wearing head mountable device 100. A closed eye, such as eye 214d, can act as a better reflector of IR radiation than an open eye. As such, IR radiation reflected to IR sensor 162 will be greater than when a wearer's eye is open, or when the eye is not present. Thus, the observed IR intensity 220d at IR sensor 162 is relatively high. Based on a relatively high IR intensity, a viewing state can be determined to be a viewing state 230d of "Wearer present with eye closed."

Figure 3A:
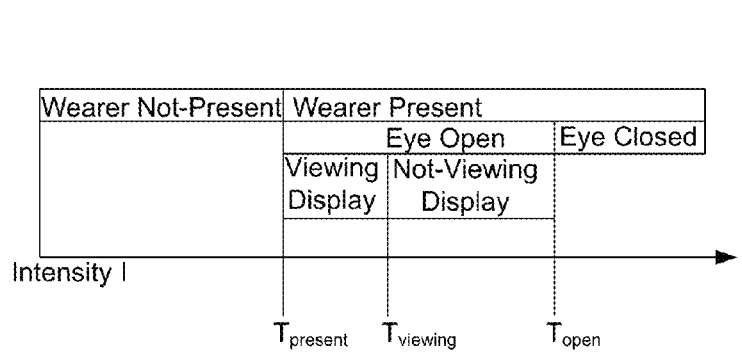
FIG. 3A is a diagram showing viewing states as a function of intensity values, according to an example embodiment.

FIG. 3A is a diagram 300 showing viewing states as a function of intensity values, according to an example embodiment. In diagram 300, intensity I of reflected IR radiation increases from left to right. FIG. 3A shows that, when I is less than a first threshold value of $T_{present}$, the viewing state is "wearer not-present" and while I is greater than or equal to $T_{present}$, the viewing state includes a "wearer present" state.

While I is greater than or equal to $T_{present}$, FIG. 3A shows that if I is less than a second threshold value, $T_{open}$, then the viewing state includes an "eye open" viewing state. Otherwise, if I is greater than or equal to $T_{open}$, then the viewing state includes an "eye closed" viewing state. Additionally, while I is greater than or equal to $T_{present}$ and less than $T_{open}$, FIG. 3A shows that if I is less than a third threshold value, $T_{viewing}$, then the viewing state includes a "viewing display" viewing state. Otherwise, I is greater than or equal to $T_{viewing}$ and the viewing state includes a "not-viewing display" viewing state.

Specific values of $T_{present}$, $T_{open}$, and/or $T_{viewing}$ can be determined using pre-determined information, such as, but not limited to, stored empirical data, data from reference sources, and/or data from other sources. In some embodiments, specific values of $T_{present}$, $T_{open}$, and/or $T_{viewing}$ can be determined using a calibration process, where a viewer is instructed to perform certain actions (e.g., take off the HMD, put on the HMD, look at the display, look away from the display, blink, etc.). During the calibration process, data related to $T_{present}$, $T_{open}$, and/or $T_{viewng}$ can be gathered and processed to determine the threshold value(s) being calibrated.

Figure 3B:
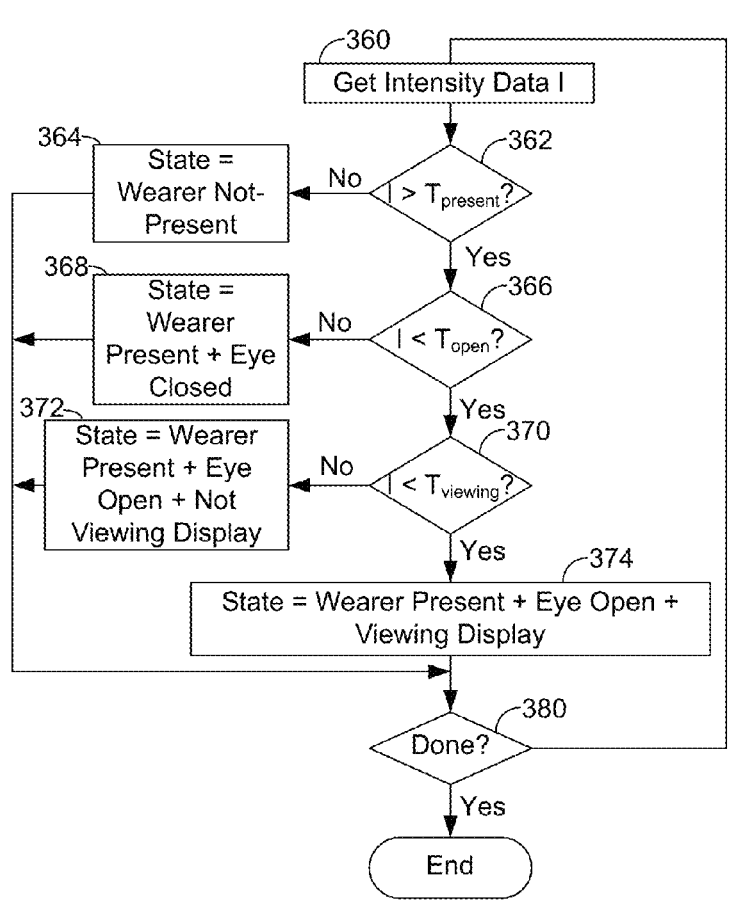
FIG. 3B is a flow chart for an example method for determining viewing states, according to an example embodiment.

FIG. 3B is a flow chart for an example method 350 for determining viewing states, according to an example embodiment.

Method 350 begins at block 360, where intensity data I is received from the IR sensor. The intensity data can include time-varying amplitude data of reflected IR radiation as received at the IR sensor.

At block 362, I is compared to the $T_{present}$ threshold. If I is less than $T_{present}$, then control proceeds to block 364; otherwise, control proceeds to block 366.

At block 364, a determination is made that the viewing state is "wearer not-present" and control proceeds to block 380.

At block 366, I is compared to the $T_{open}$ threshold. If I is less than $T_{open}$, then control proceeds to block 368; otherwise, control proceeds to block 370.

At block 368, a determination is made that the viewing state is "wearer present" and "eye closed" and control proceeds to block 380.

At block 370, I is compared to the $T_{viewing}$ threshold. If I is less than $T_{viewing}$, then control proceeds to block 372; otherwise, control proceeds to block 374.

At block 372, a determination is made that the viewing state is "wearer present", "eye open", and "not viewing display" and control proceeds to block 380.

At block 374, a determination is made that the viewing state is "wearer present" "eye open", and "viewing display" and control proceeds to block 380.

At block 380, a determination is made as to whether method 350 is completed. If method 350 is determined not to be completed, control proceeds to block 360. Otherwise, method 350 is terminated.

Blink durations can be calculated from a given sequence of viewing states and corresponding times. For example, suppose that viewing states are determined using method 350, or some equivalent method, for amplitude data of reflected IR radiation collected every T seconds; e.g., T≤0.25. An example set of viewing states can then be generated as shown in Table 2 below, for T=0.1 seconds, starting at a time T1.

TABLE 2

| Time | Viewing State | Open/Closed Transition |
| --- | --- | --- |
| T1 | Wearer present + eye open + viewing display | |
| T1 + 0.1 sec. | Wearer present + eye closed | Open to Closed |
| T1 + 0.2 sec. | Wearer present + eye closed | |
| T1 + 0.3 sec. | Wearer present + eye open + viewing display | Closed to Open |
| T1 + 0.4 sec. | Wearer present + eye open + viewing display | |
| T1 + 0.5 sec. | Wearer present + eye open + not viewing display | |
| T1 + 0.6 sec. | Wearer present + eye open + not viewing display | |
| T1 + 0.7 sec. | Wearer present + eye open + viewing display | |
| T1 + 0.8 sec. | Wearer present + eye open + viewing display | |
| T1 + 0.9 sec. | Wearer present + eye open + viewing display | |
| T1 + 1.0 sec. | Wearer present + eye open + viewing display | |
| T1 + 1.1 sec. | Wearer present + eye closed | Open to Closed |
| T1 + 1.2 sec. | Wearer present + eye closed | |
| T1 + 1.3 sec. | Wearer present + eye closed | |
| T1 + 1.4 sec. | Wearer present + eye closed | |
| T1 + 1.5 sec. | Wearer present + eye open + viewing display | Closed to Open |

Table 2 shows transitions between an eye-open related viewing state and an eye-closed related viewing state. For example, at time T1, the viewing state is shown as "Wearer present+eye open+viewing display" and at T1+0.1 sec., the viewing state is shown as "Wearer present+eye closed." Based on these two viewing states, a transition between an eye of the wearer being open at time T1 and being closed at time T1+0.1 sec. can be detected. Table 2 shows this transition as an "Open to Closed" transition at time T1+0.1 sec.

Table T2 shows at time T1+0.2 sec., the viewing state is shown as "Wearer present+eye closed" and at T1+0.3 sec., the viewing state is shown as "Wearer present+eye open+viewing display." Based on these two viewing states, a transition between the eye of the wearer being closed at time T1+0.2 sec. and being open at time T1+0.3 sec. can be detected. Table 2 shows this transition as a "Closed to Open" transition at time T1+0.3 sec.

Using the terminology shown in Table 2, a blink can be defined as an "Open to Closed" transition followed by a "Closed to Open" transition. Then, a blink duration B can be defined as a time when a "Closed to Open" transition is detected minus a time when an "Open to Closed" transition is detected. In this example, blink duration B=T1+0.3−(T1+0.1)=0.2 sec. Table 2 also shows an "Open to Closed" transition at T1+1.1 sec. and "Closed to Open" transition at T1+1.5 sec. In this example, blink duration B=T1+1.5−(T1+1.1)=0.4 seconds.

This sequence of viewing states and corresponding blink durations can be used to control the head mountable display. For example, a user interface can receive viewing state data, such as shown above in Table 2, and act in accordance with viewing states, blinks, and blink durations, as discussed below in detail in the context of FIGS. 5A-5E.

Figure 4A:
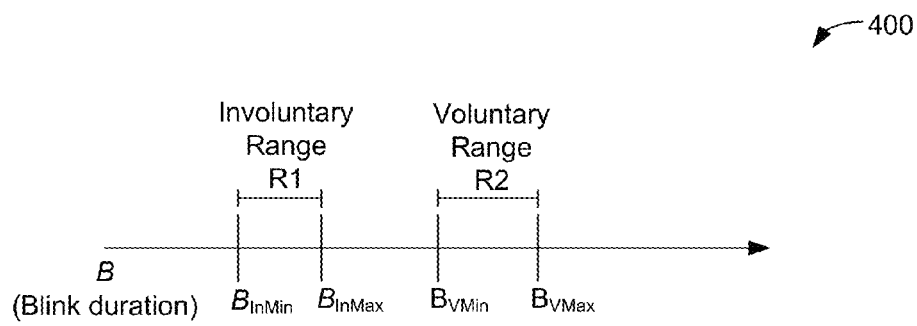
FIG. 4A is a diagram showing ranges of blink durations, according to an example embodiment.

FIG. 4A is a diagram 400 showing ranges of blink durations, according to an example embodiment. In diagram 400, a blink duration B, or duration of time a person keeps their eyes closed during a blink, increases from left to right. Diagram 400 shows two blink duration ranges: an involuntary range R1 and a voluntary range R2. Involuntary blinks can include blinks performed to keep the surface of the eye moist and/or to otherwise protect the eye. Typically, involuntary blinks are performed reflexively without conscious decision. In contrast, voluntary blinks can be consciously performed by the wearer.

Typically, voluntary blinks take longer than involuntary blinks FIG. 4A shows R1 as a range of blink durations for involuntary blinks, beginning at an involuntary minimum blink duration $B_{InMin}$, and ending at an involuntary maximum blink duration $B_{InMax}$. FIG. 4A shows R2 as a range of blink durations for voluntary blinks, beginning at a voluntary minimum blink duration $B_{VMin}$, and ending at a voluntary maximum blink duration $B_{VMax}$.

Specific values of $B_{InMin}$, $B_{InMax}$, $B_{VMin}$, and/or $B_{vMax}$ can be determined using pre-determined information, such as, but not limited to, stored empirical data, data from reference sources, and/or data from other sources. In some embodiments, specific values of $B_{InMin}$, $B_{InMax}$, $B_{VMin}$, and/or $B_{VMax}$ can be determined using a calibration process, where a viewer is instructed to perform certain actions (e.g., wear the HMD for a period of time to detect involuntary blinks, blink a number of times in succession, etc.). During the calibration process, data, such as blink durations related to $B_{InMin}$, $B_{InMax}$, $B_{VMin}$, and/or $B_{VMax}$ can be gathered and processed to determine the threshold value(s) being calibrated.

Figure 4B:
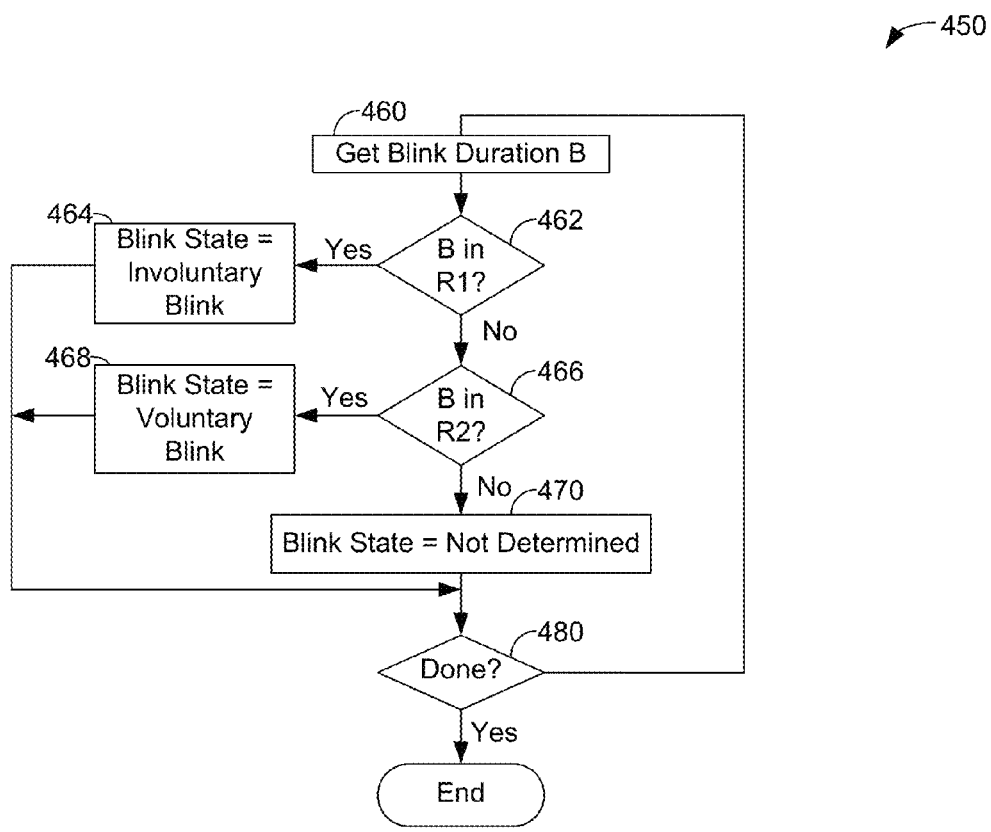
FIG. 4B is a flow chart for an example method for determining blink states, according to an example embodiment.

FIG. 4B is a flow chart for an example method 450 for determining blink states, according to an example embodiment. Given a blink duration and the ranges shown in FIG. 4A, a blink can be classified as having one of three blink states: an involuntary blink, a voluntary blink, or a not-determined blink.

Method 450 begins at block 460, where a blink duration value B is received.

At block 462, B is compared to the R1 range. If B is within R1, that is, $B_{VMin} \leq B \leq B_{VMax}$, then control proceeds to block 464; otherwise, control proceeds to block 466.

At block 464, a determination is made that the blink state is an "involuntary blink" and control proceeds to block 480.

At block 462, B is compared to the R2 range. If B is within R2, that is, $B_{VMin} \leq B \leq B_{VMax}$, then control proceeds to block 468; otherwise, control proceeds to block 470.

At block 468, a determination is made that the blink state is a "voluntary blink" and control proceeds to block 480.

At block 468, a determination is made that the blink state is "not determined" and control proceeds to block 480. In some embodiments not shown in FIG. 4B, when the blink state is not determined, the blink duration can be compared to other ranges of blink durations to characterize the blink determination, such as a "slow voluntary blink" range, a "dozing" range, and/or a "sleeping" range, among others.

At block 480, a determination is made as to whether method 450 is completed. If method 450 is determined not to be completed, control proceeds to block 460. Otherwise, method 450 is terminated.

Example User Interface Scenario

FIGS. 5A through 5E show example scenario 500 using viewing states and blink states to generate user interface commands, in accordance with an example embodiment.

Scenario 500 begins with a wearer 510 named Joe using a video camera application of HMD 100 that is equipped to perform in accordance with viewing states and blink states. During scenario 500, wearer 510 looks at the display to record, blinks to toggle between video-only recording and audio-video recording, and takes off HMD 100 to terminate the video camera application.

Figure 5A:
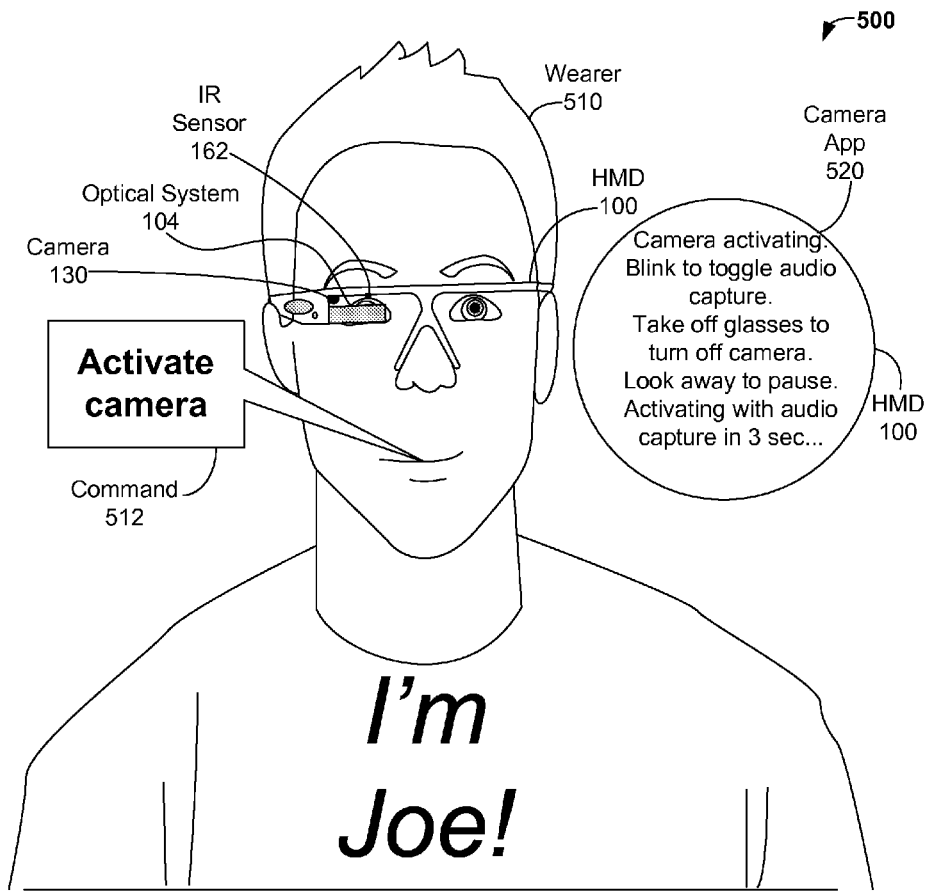
FIGS. 5A through 5E show an example scenario using viewing states and blink states to generate user interface commands, in accordance with an example embodiment.

FIG. 5A shows wearer 510, named Joe, wearing HMD 100 equipped with optical system 104 and IR sensor 162 to determine viewing and blink states. In scenario 500, HMD 100 is additionally equipped at least with a video camera application that controls camera 130. Scenario 500 begins with wearer 510 activating the video camera application via speech command 512 of "Activate camera." In other scenarios, one or more user interfaces other than a speech interface can be used to activate the video camera application, such as, but not limited to, a touch-based user interface such as a touch pad or keyboard, viewing-state and blink-state-based user interface, and/or a gaze-based user interface.

The video camera application of scenario 500 is configured to receive viewing state and blink state information and generate user interface commands based on the viewing and blink states. FIG. 5A shows that camera application 520 can detect a voluntary blink "to toggle audio capture", detect a wearer not-present state "to turn off camera", and detect a not-viewing display state "to pause."

Figure 5B:
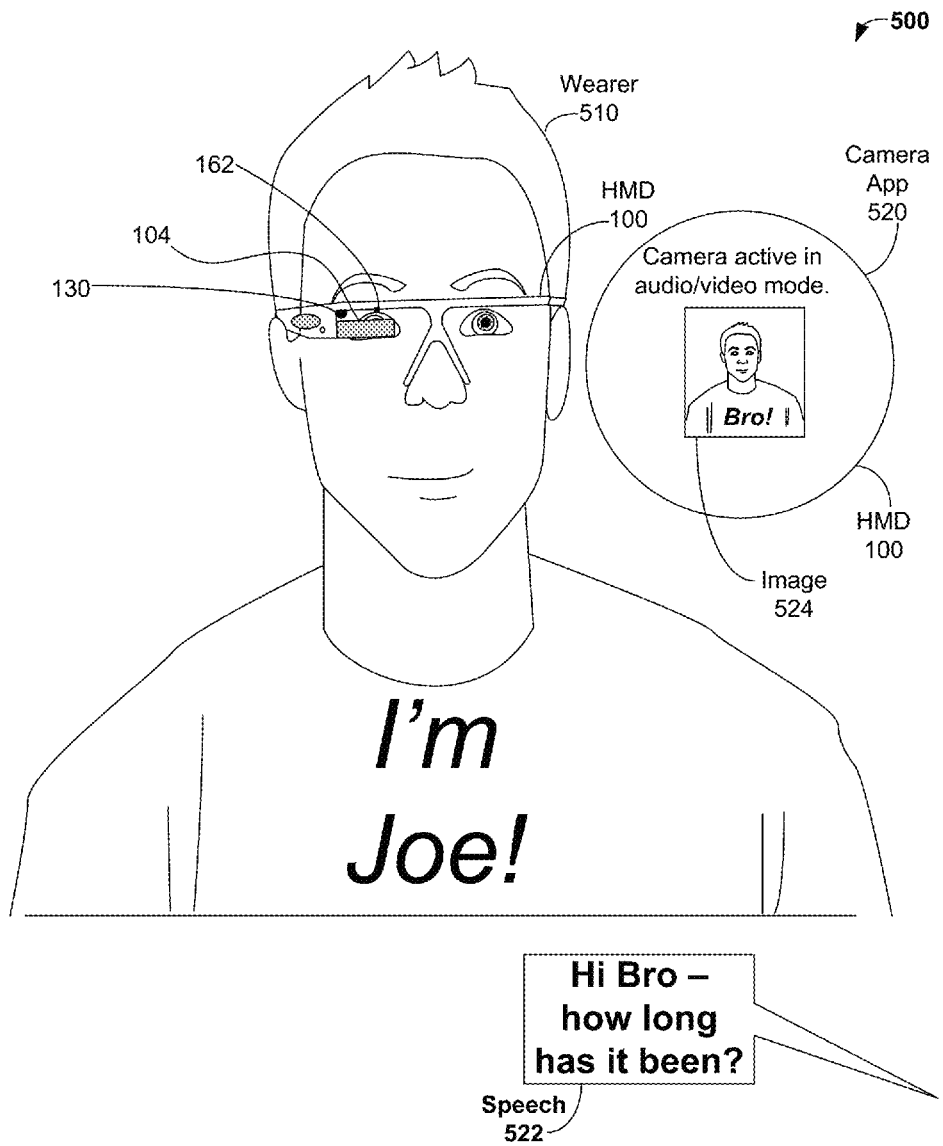

Scenario 500 continues on FIG. 5B where Joe's conversation partner, Bro, utters speech 522 of "Hi Bro—how long has it been?" During this interval, camera application 520 has informed wearer 510 of HMD 100 that the camera is "active in audio/video mode" and shown image 524 of a capture from camera 130. FIG. 5B shows that image 524 is a picture of Bro.

Figure 5C:
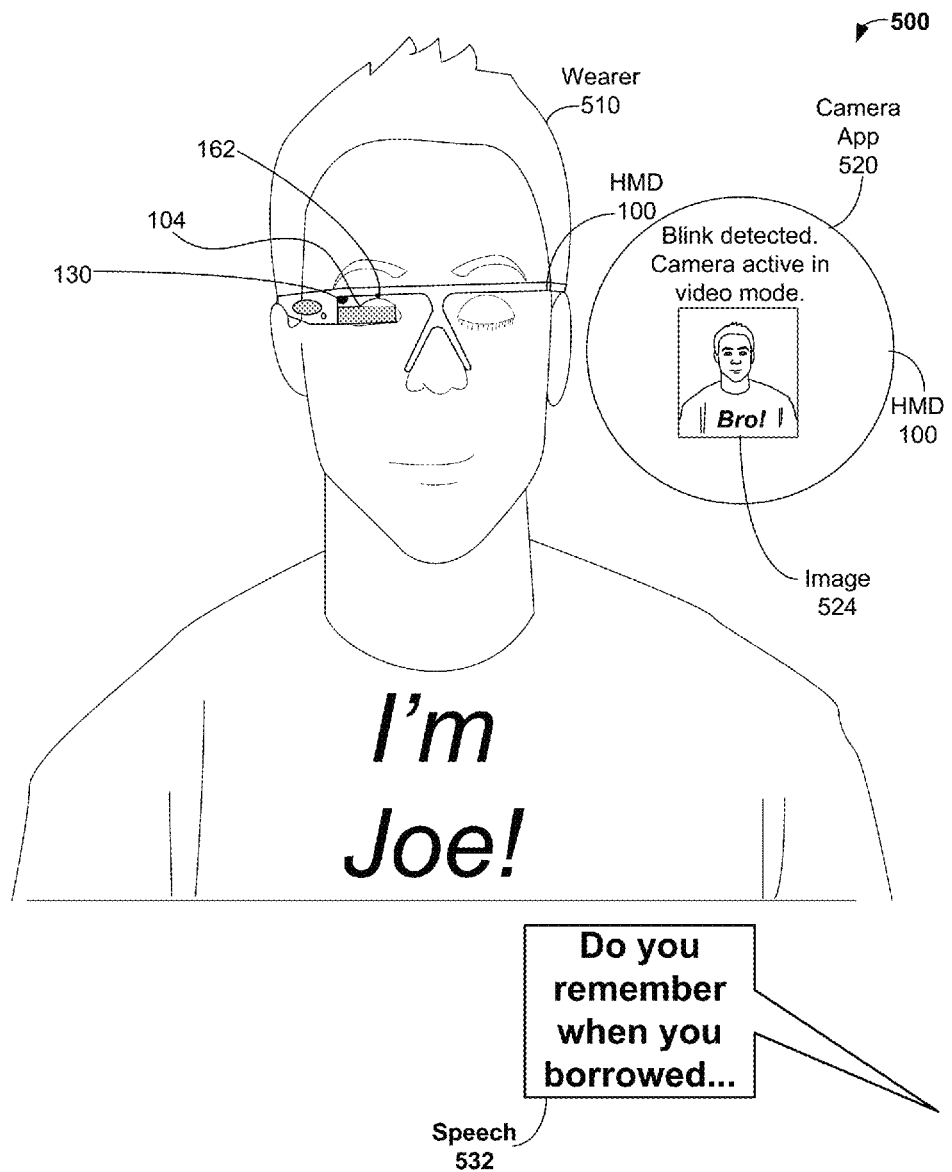

Scenario 500 continues on FIG. 5C with Bro uttering speech 532 of "Do you remember when you borrowed . . ." Upon hearing speech 532, wearer 510 decides to toggle the audio recording feature of camera application 520 by blinking FIG. 5C shows camera application 520 having detected a voluntary blink by wearer 510 and, in response, setting the "camera [to be] active in video mode" and continuing to display captured images taken by camera 130.

Figure 5D:
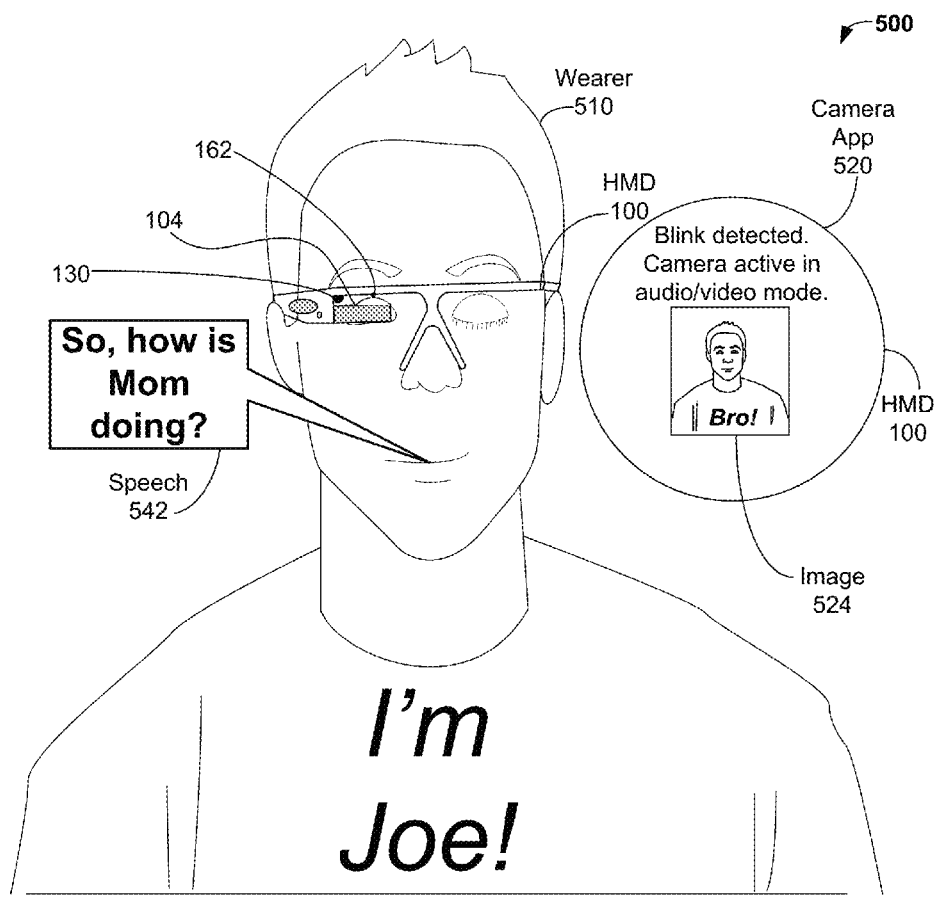

In scenario 500, Joe then asks Bro "how is Mom doing?" via speech 542 as shown in FIG. 5D. While uttering speech 542, wearer 510 decides to toggle the audio recording feature of camera application 520 by blinking FIG. 5D shows camera application 520 having detected a voluntary blink by wearer 510 and, in response, setting the "camera [to be] active in audio/video mode" and continuing to display captured images taken by camera 130.

Figure 5E:
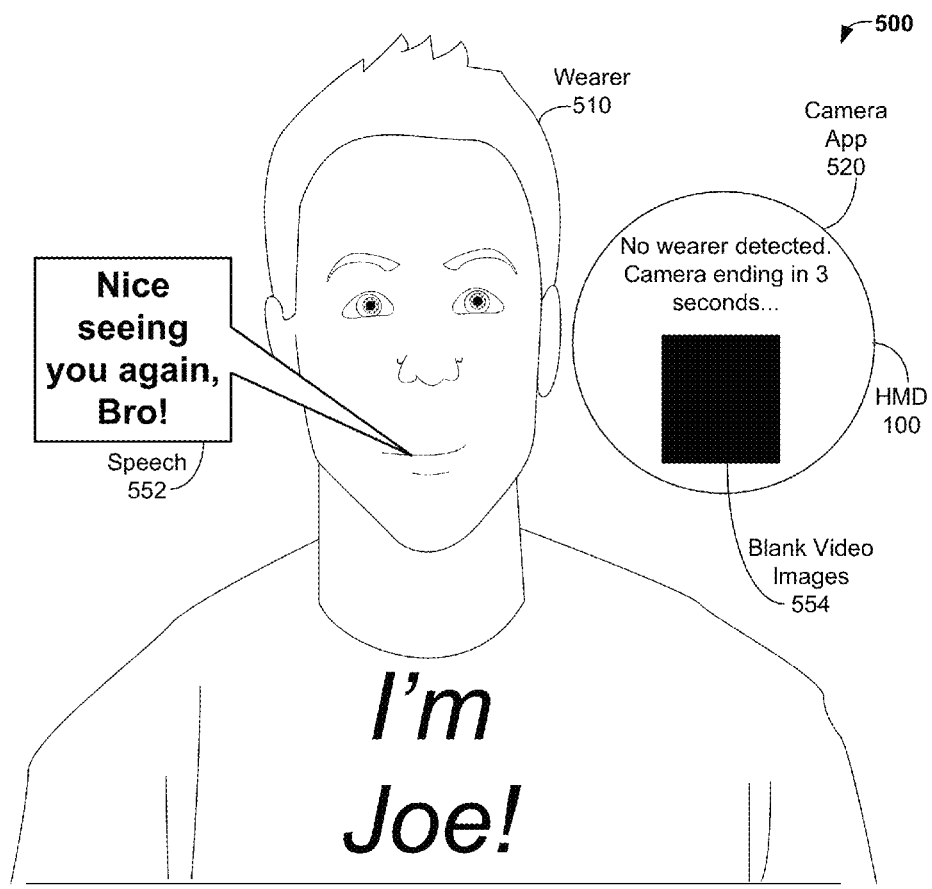

Scenario 500 concludes with wearer 510 removing HMD 100 and uttering speech 552 of "Nice seeing you again, Bro!" as shown in FIG. 5E. In response, speech application 520 detects the wearer not-present state of HMD 100 and starts a shutdown procedure, perhaps to give wearer 510 a short time to restart camera application 520 by putting on HMD 100 again.

FIG. 5E shows that camera application 520 has indicated that no wearer is detected and so is "ending in 3 seconds." During this interval, camera application 520 does not capture data from camera 130; rather, as shown in FIG. 5E, blank video images 554 are added to the stored video instead. In other embodiments, camera application 520 can capture images from camera 130 until camera application 520 terminates. Scenario 500 ends with camera application 520 terminating after the 3-second interval accorded by the shutdown procedure.

Many other example scenarios, user interfaces, user interface commands, and uses of viewing states and/or blink states are possible as well.

Example Methods for Determining Viewing States

Figure 6:
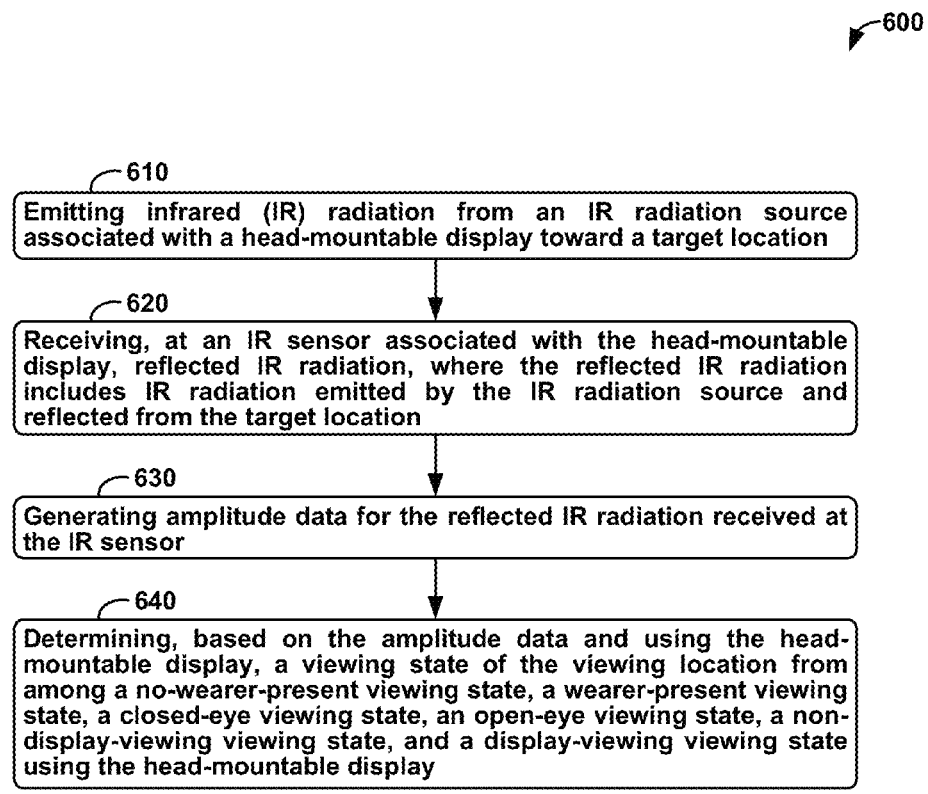
FIG. 6 is a flow chart for another example method, according to an example embodiment.

FIG. 6 is a flow chart illustrating a method according to an example embodiment. Method 600 is described by way of example as being carried out by a computing device, such as one or more of the head mountable devices described herein, but may be partially or completely carried out by other devices or systems as well.

Method 600 may be implemented to determine a viewing state at a target location. Method 600 begins at block 610, where a head-mountable display can emit IR radiation (a.k.a. IR light) from an associated IR radiation source toward a target location. The head-mountable display can include an optical system, where the optical system can include an IR radiation source configured to emit IR radiation and a display light source configured to emit visible light toward the target location. The optical system can be configured so that the IR radiation and the visible light follow a common path to the target location. In some embodiments, the IR sensor can be configured to be physically separate from the optical system.

At block 620, an IR sensor associated with the head-mountable display can receive reflected IR radiation. The reflected IR radiation can include IR radiation emitted by the IR radiation source and reflected from the target location.

At block 630, amplitude data can be generated for the reflected IR radiation.

At block 640, the head-mountable display can be used to determine a viewing state of the target location. The viewing state can be based on the amplitude data. The viewing state can determined from among a no-wearer-present viewing state, a wearer-present viewing state, a closed-eye viewing state, an open-eye viewing state, a non-display-viewing viewing state, and a display-viewing viewing state.

In some embodiments, determining the viewing state of the target location can include comparing the amplitude data to calibration data corresponding to a plurality of viewing states.

In some embodiments, method 600 can further include generating a user-interface command for the head-mountable display based on the viewing state.

In particular embodiments, method 600 can further include: (a) generating time-varying amplitude data for the reflected IR radiation received at the IR sensor, (b) determining a sequence of viewing states of the target location based on the time-varying amplitude data, and (c) controlling the head-mountable display based on the sequence of viewing states. In some of the particular embodiments, the sequence of viewing states can include a first viewing state at a first time and a second viewing state at a second time. The second time can be after the first time. Then, controlling the head-mountable display based on the sequence of viewing states can include generating a user-interface command for the head-mountable display, in response to the second viewing state differing from the first viewing state.

In other of the particular embodiments, the sequence of viewing states can include a first viewing state at a first time and a second viewing state at a second time. The second time can be after the first time. Then, controlling the head-mountable display based on the sequence of viewing states can include generating a user-interface command for the head-mountable display, in response to the second viewing state equaling the first viewing state.

CONCLUSION

Example methods and systems are described herein. It should be understood that the word "exemplary" is used herein to mean "serving as an example, instance, or illustration." Any embodiment or feature described herein as "exemplary" is not necessarily to be construed as preferred or advantageous over other embodiments or features. The example embodiments described herein are not meant to be limiting. It will be readily understood that certain aspects of the disclosed systems and methods can be arranged and combined in a wide variety of different configurations, all of which are contemplated herein.

The above detailed description describes various features and functions of the disclosed systems, devices, and methods with reference to the accompanying figures. In the figures, similar symbols typically identify similar components, unless context dictates otherwise. The illustrative embodiments described in the detailed description, figures, and claims are not meant to be limiting. Other embodiments can be utilized, and other changes can be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the ladder diagrams, scenarios, and flow charts in the figures and as discussed herein, each block and/or communication may represent a processing of information and/or a transmission of information in accordance with example embodiments. Alternative embodiments are included within the scope of these example embodiments. In these alternative embodiments, for example, functions described as blocks, transmissions, communications, requests, responses, and/or messages may be executed out of order from that shown or discussed, including substantially concurrent or in reverse order, depending on the functionality involved. Further, more or fewer blocks and/or functions may be used with any of the ladder diagrams, scenarios, and flow charts discussed herein, and these ladder diagrams, scenarios, and flow charts may be combined with one another, in part or in whole.

A block that represents a processing of information may correspond to circuitry that can be configured to perform the specific logical functions of a herein-described method or technique. Alternatively or additionally, a block that represents a processing of information may correspond to a module, a segment, or a portion of program code (including related data). The program code may include one or more instructions executable by a processor for implementing specific logical functions or actions in the method or technique. The program code and/or related data may be stored on any type of computer readable medium such as a storage device including a disk or hard drive or other storage medium.

The computer readable medium may also include non-transitory computer readable media such as computer-readable media that stores data for short periods of time like register memory, processor cache, and random access memory (RAM). The computer readable media may also include non-transitory computer readable media that stores program code and/or data for longer periods of time, such as secondary or persistent long term storage, like read only memory (ROM), optical or magnetic disks, compact-disc read only memory (CD-ROM), for example. The computer readable media may also be any other volatile or non-volatile storage systems. A computer readable medium may be considered a computer readable storage medium, for example, or a tangible storage device.

Moreover, a block that represents one or more information transmissions may correspond to information transmissions between software and/or hardware modules in the same physical device. However, other information transmissions may be between software modules and/or hardware modules in different physical devices.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A method, comprising:
   initiating, by a head-mountable device, a camera application;
   receiving, by the head-mountable device, first audio data that is generated by an audio sensor associated with the head-mountable device;
   detecting that the first audio data includes a speech command that corresponds to a video recording process;
   in response to the speech command, initiating the video recording process via the camera application, wherein the video recording process comprises capturing second audio data and video data and storing the second audio data and the video data to a video file;
   emitting infrared (IR) radiation from an IR radiation source associated with the head-mountable device toward a target location;
   receiving, at an IR sensor associated with the head-mountable device, reflected IR radiation, wherein the reflected IR radiation comprises IR radiation emitted by the IR radiation source and reflected from the target location;
   generating time-varying amplitude data for the reflected IR radiation received at the IR sensor;
   determining, based on the time-varying amplitude data, a sequence of viewing states of the target location; and
   during the video recording process:
   (a) detecting, in the sequence of viewing states, a portion of the sequence corresponding to an eye closure of a first duration;

(b) determining that the first duration is within a first range of durations corresponding to a voluntary blink, wherein the durations in the first range are longer than durations in a second range of durations corresponding to an involuntary blink; and (c) in response to determining that the first duration is within the first range of durations corresponding to a voluntary blink, ceasing the capturing of second audio data and continuing the capturing and storing of video data to the video file.

2. The method of claim 1, wherein determining the sequence of viewing states of the target location comprises:
comparing the time-varying amplitude data to calibration data corresponding to a plurality of viewing states.

3. The method of claim 1, further comprising:
controlling the head-mountable device based on the sequence of viewing states.

4. The method of claim 3, wherein the sequence of viewing states comprises a first viewing state at a first time and a second viewing state at a second time, wherein the second time is after the first time, and wherein controlling the head-mountable device based on the sequence of viewing states comprises:
in response to the second viewing state differing from the first viewing state, generating a command for the head-mountable device.

5. The method of claim 3, wherein the sequence of viewing states comprises a first viewing state at a first time and a second viewing state at a second time, wherein the second time is after the first time, and wherein controlling the head-mountable device based on the sequence of viewing states comprises:
in response to the second viewing state equaling the first viewing state, generating a command for the head-mountable device.

6. An article of manufacture including a non-transitory computer-readable medium having instructions stored thereon that, upon execution of the instructions by a computing device, cause the computing device to perform functions comprising:
initiating a camera application associated with a head-mountable device;
receiving first audio data that is generated by an audio sensor associated with the head-mountable device;
detecting that the first audio data includes a speech command that corresponds to a video recording process;
in response to the speech command, initiating the video recording process via the camera application, wherein the video recording process comprises capturing second audio data and video data and storing the second audio data and the video data to a video file;
emitting infrared (IR) radiation from an IR radiation source associated with the head-mountable device toward a target location;
receiving, at an IR sensor associated with the head-mountable device, reflected IR radiation, wherein the reflected IR radiation comprises IR radiation emitted by the IR radiation source and reflected from the target location;
generating time-varying amplitude data for the reflected IR radiation;
determining, based on the time-varying amplitude data, a sequence of viewing states of the target location; and
during the video recording process:
(a) detecting, in the sequence of viewing states, a portion of the sequence corresponding to an eye closure of a first duration;
(b) determining that the first duration is within a first range of durations corresponding to a voluntary blink, wherein the durations in the first range are longer than durations in a second range of durations corresponding to an involuntary blink; and
(c) in response to determining that the first duration is within the first range of durations corresponding to a voluntary blink, ceasing the capturing of second audio data and continuing the capturing and storing of video data to the video file.

7. The article of manufacture of claim 6, wherein determining the sequence of viewing states of the target location comprises:
comparing the time-varying amplitude data to calibration data corresponding to a plurality of viewing states.

8. The article of manufacture of claim 6, further comprising:
controlling the head-mountable device based on the sequence of viewing states.

9. The article of manufacture of claim 8, wherein the sequence of viewing states comprises a first viewing state at a first time and a second viewing state at a second time, wherein the second time is after the first time, and wherein controlling the head-mountable device based on the sequence of viewing states comprises:
in response to the second viewing state differing from the first viewing state, generating a command for the head-mountable device.

10. The article of manufacture of claim 8, wherein the sequence of viewing states comprises a first viewing state at a first time and a second viewing state at a second time, wherein the second time is after the first time, and wherein controlling the head-mountable device based on the sequence of viewing states comprises:
in response to the second viewing state equaling the first viewing state, generating a command for the head-mountable device.

11. A head-mountable device, comprising:
a head-mountable display;
an audio sensor;
an infrared (IR) radiation source, configured to emit IR radiation toward a target location;
an IR sensor configured to receive IR radiation reflected from the target location and to generate time-varying amplitude data for the reflected IR radiation; and
a processor, configured to:
initiate a camera application;
receive first audio data that is generated by the audio sensor;
detect that the first audio data includes a speech command that corresponds to a video recording process;
in response to the speech command, initiate the video recording process via the camera application, wherein the video recording process comprises capturing second audio data and video data and storing the second audio data and the video data to a video file;
receive the time-varying amplitude data;
determine, based on the time-varying amplitude data, a sequence of viewing states of the target location; and
during the video recording process:
(a) detect, in the sequence of viewing states, a portion of the sequence corresponding to an eye closure of a first duration;
(b) determine that the first duration is within a first range of durations corresponding to a voluntary blink, wherein the durations in the first range are longer than durations in a second range of durations corresponding to an involuntary blink; and (c) in response to determining that the first duration is within the first range of durations corresponding to a voluntary blink, cease the capturing of second audio data and continuing the capturing and storing of video data to the video file.

12. The head-mountable device of claim 11, wherein the processor is configured to determine the sequence of viewing states of the target location by at least:

comparing the time-varying amplitude data to calibration data corresponding to a plurality of viewing states.

13. The head-mountable device of claim 11, wherein the processor is further configured to:

control the head-mountable display based on the sequence of viewing states.

14. The head-mountable device of claim 13, wherein the sequence of viewing states comprises a first viewing state at a first time and a second viewing state at a second time, wherein the second time is after the first time, and wherein the processor is configured to control the head-mountable display based on the sequence of viewing states by generating a command for the head-mountable display in response to the second viewing state differing from the first viewing state.

15. The head-mountable device of claim 13, wherein the sequence of viewing states comprises a first viewing state at a first time and a second viewing state at a second time, wherein the second time is after the first time, and wherein the processor is configured to control the head-mountable display based on the sequence of viewing states by generating a command for the head-mountable display in response to the second viewing state equaling the first viewing state.

16. The head-mountable device of claim 11, further comprising an optical system, the optical system comprising the IR radiation source and a display light source configured to emit visible light toward the target location and wherein the optical system is configured so that the IR radiation and the visible light follow a common path to the target location.

17. The head-mountable device of claim 16, wherein the IR sensor is configured to be physically separate from the optical system.

18. The head-mountable device of claim 11, wherein the sequence of viewing states of the target location comprises viewing states from among a no-wearer-present viewing state, a wearer-present viewing state, a closed-eye viewing state, an open-eye viewing state, a non-display-viewing viewing state, and a display-viewing viewing state.

* * * * *